(12) United States Patent
Waldorf et al.

(10) Patent No.: US 7,798,643 B2
(45) Date of Patent: Sep. 21, 2010

(54) SYSTEM FOR ANALYZING EYE RESPONSES TO AUTOMATICALLY TRACK SIZE, LOCATION, AND MOVEMENT OF THE PUPIL

(75) Inventors: Ronald Waldorf, Beverly Hills, CA (US); Barbara Mauch, Inglewood, CA (US)

(73) Assignee: Visionetx, Inc., Centennial, CO (US)

( * ) Notice: Subject to any disclaimer, the term of this patent is extended or adjusted under 35 U.S.C. 154(b) by 424 days.

(21) Appl. No.: 11/934,414

(22) Filed: Nov. 2, 2007

(65) Prior Publication Data

US 2009/0115965 A1    May 7, 2009

(51) Int. Cl.
*A61B 3/14*     (2006.01)
(52) U.S. Cl. .................. 351/209; 351/210; 351/246
(58) Field of Classification Search .......... 351/209, 351/210, 211, 212, 221, 246, 205, 247
See application file for complete search history.

(56) References Cited

U.S. PATENT DOCUMENTS

| 5,137,345 A | 8/1992 | Waldorf et al. |
| 5,684,562 A * | 11/1997 | Fujieda ............... 351/212 |
| 6,193,373 B1 * | 2/2001 | Apple et al. .......... 351/221 |

* cited by examiner

*Primary Examiner*—Hung X Dang
(74) *Attorney, Agent, or Firm*—Patton Boggs LLP (57) ABSTRACT

The present system for analyzing eye responses accurately and automatically tracks the size, location, and movement of a subject's pupil(s) in response to a predetermined test protocol. These eye responses include both ocularmotor and pupillary responses to illumination and target tracking for either eye or both eyes simultaneously. The series of digital image frames of a subject's eyes, taken during the execution of a predetermined stimulus protocol, are automatically processed to determine pupil location, size, and responsiveness to changes in illumination.

16 Claims, 4 Drawing Sheets

SYSTEM FOR ANALYZING EYE RESPONSES TO AUTOMATICALLY TRACK SIZE, LOCATION, AND MOVEMENT OF THE PUPIL

FIELD OF THE INVENTION

This invention relates to a system for non-invasively tracking the size, location, and movement of a subject's pupil.

BACKGROUND OF THE INVENTION

It is a problem to accurately and automatically track the size, location, and movement of a subject's pupil(s) in response to predetermined stimuli. These measurements have use in various applications, and one of particular interest is to determine whether a subject is impaired, regardless of whether this is due to a medical condition, or the use of alcohol or drugs, or whether the subject is suffering from sleep deprivation or any other condition which interferes with the subject's ability to perform their assigned tasks. This is particularly a problem in the workplace where an employee who is presently functioning at a level of alertness that is less than their norm can place themselves and others in danger of injury, especially when the impaired employee is operating machinery. In addition, an impaired employee functions at a reduced level of efficiency and evidences a dramatic increase in the incidence of errors in the impaired employee's work product There have been some previous computer-based attempts to automate the pupil detection and tracking process to quickly determine the exact area of a subject's pupil. These proposed processes have relied on either finding the darkest area on the image of the eye and then thresholding within a range of this value to extract the pupil, or by attempting to fit an ellipse of predetermined diameter to the features present in the input image. Both approaches fail at producing an exact measurement of the pupil's location and area when light specularities or long eyelashes occlude the pupil, and when other dark regions are detected in addition to or instead of the pupil due to the presence of heavy eye makeup or bushy eyebrows. These complex conditions cause the subject's pupil to have a non-circular shape, which would be deformed by the ellipse-fitting eye-response tracking process normally used to detect pupils and irises in human eyes; and other approaches based on the detection of the darkest point in the image would fail in the presence of eye makeup or thick eyebrows. These methods also have no means to compensate for specularities that can occur due to the lighting conditions. Thus, there presently does not exist a system to accurately and automatically track the area and location of a subject's pupil(s) in response to predetermined stimuli.

This problem of accurate pupil location extends into the field of impairment testing where presently there is no automated system for quickly and accurately determining the impairment of large numbers of employees, so employers resort to random and expensive drug testing to detect chemicals in the employees' urine, thereby identifying employees in the workplace who have used certain identified drugs. While this approach fails to provide any degree of effective screening of the entire workforce on a daily basis, it is expected that it does have some deterrent effect which decreases the incidence of impaired employees.

It is known that the determination of a subject's impairment can be accomplished by the measurement of the subject's eye gaze tracking and the monitoring of the subject's eye behavior, which measurements are compared to a normal response for the subject to determine a subject's alertness and attention. For example, by tracking and measuring the pupil responses of the subject, it is possible to determine the subject's impairment, since abnormal pupil dilation and pupil movement in response to a stimulus are involuntary responses. These responses, in association with eye movement in tracking a visual stimulus, can definitively determine impairment in a subject.

With all of these metrics available as impairment determination tools, the accurate measurement and tracking of the subject's pupil centroid location and determination of the area of the pupil are critical to the precise determination of impairment. It is also important to detect eye blinking in order to ensure that pupil measurements are not computed at those time instances when a blink occurs, since the pupil is either partially visible or not visible at all when a blink occurs.

Presently, for impairment testing, all of these measurements are performed manually, with the accuracy and reliability of these measurements being subjective and possibly tainted by the ambient conditions under which the test is administered. Ambient conditions include the inability to maintain the subject's gaze in a fixed direction, erratic lighting conditions, and the subjective nature of the test administrator's administration of the test.

Therefore, presently there is no viable automated system that can accurately track and report into analysis software the location and movement of a subject's pupil(s).

BRIEF SUMMARY OF THE INVENTION

The above-described problems are solved and a technical advance achieved by the present system for analyzing eye responses to accurately and automatically track the size, location, and movement of a subject's pupil(s) in response to a predetermined test protocol (termed "pupil tracking system" herein). These measurements have use in various applications, and one of particular interest is to automatically determine impairment of a subject. These eye responses include both ocularmotor and pupillary responses to illumination and target tracking for either eye or both eyes simultaneously. The pupil tracking system uses a series of digital image frames of a subject's eyes, taken during the execution of a predetermined test protocol, which digital image frames are automatically processed to determine pupil location, size, and responsiveness to changes in illumination.

The pupil tracking system obtains a series of digital image frames from a user interface device, which digital image frames capture pupil location and size in response to the execution of a predetermined test protocol on the subject. A typical user interface device, known as an Ocular Motor Module (OMM), is illustrated in U.S. Pat. No. 5,137,345 and can be used to generate these digital image frames. This user interface device, for example, has light emitting diodes (LEDs) in place to act as the stimulus for left/right, up/down, and bright/dim activity. Cameras (and associated infrared lights) capture the subject's eye movements, as driven by the test protocol, and the resulting image frames are digitized for analysis by the pupil tracking system. The horizontal, vertical, and oblique eye movement and eye lid blink activity, as well as the size and reactivity of the pupil, are the primary data that can be retrieved from the sequence of digital images. Thus, monitoring the subject's ocularmotor and pupillary responses enables the pupil tracking system to determine the pupil area and location which can be used, for example, to determine a subject's alertness and attention.

The present pupil tracking system uses a method for quickly and accurately localizing the subject's pupils, as well as their boundaries, area, and center coordinates. The pupil tracking system receives a series of digital image frames of the subject's eyes and uses a region-growing, eye-response tracking process to extract and track the centroid location and area of the subject's pupil(s) under difficult conditions, such as blinking, eyelid droop, head movement, eye gaze at the extreme corners of the eyes, presence of heavy eye makeup, and where light specularities occur in or near the pupil region. The eye-response tracking process applies morphological filtering to remove light specularities, thereby compensating for them in the final computation of the pupil area and centroid location. The pupil then is extracted by applying a region-growing procedure to accurately extract the pupil's shape. The geometric properties of the extracted region are used to determine if the pupil measurements should be accepted or discarded. Blinks are detected by monitoring changes in the intensity distribution from frame to frame, so that those frames containing a blink may be eliminated from processing. This ensures that only samples with a high confidence and reliability are considered in the generation of pupil location and movement data.

This eye-response tracking process thereby produces pupil area and location data which can be used, for example, to determine the subject's awareness and impairment by automatically monitoring the subject's ocular responses to the execution of a predetermined test protocol. The fundamental characteristics of the present eye-response tracking process are: (1) it is able to eliminate multiple light specularities from the eye; (2) it can accurately detect and compute the properties of the pupil even in the presence of heavy eye make up, long occluding eyelashes, and droopy eyelids; (3) it predicts the future position of the pupil based on the previous position (i.e., the pupil centroid location found in the previous frame is used to seed the region-growing eye-response tracking process in the next frame); and (4) it detects and disregards eye blinks (i.e., samples are discarded from consideration in determination decisions). This eye-response tracking process provides robust eye tracking technology with accuracy, precision, and speed.

DETAILED DESCRIPTION OF THE INVENTION

Throughout this application, reference is made to the effects of impairment by drugs. It is understood the term "drugs" includes not only medicinal substances and addictive narcotics, but also is to be understood to include any other ingested substance which affects the brain, such as alcoholic beverages and the like.

System Characteristics

Figure 1:
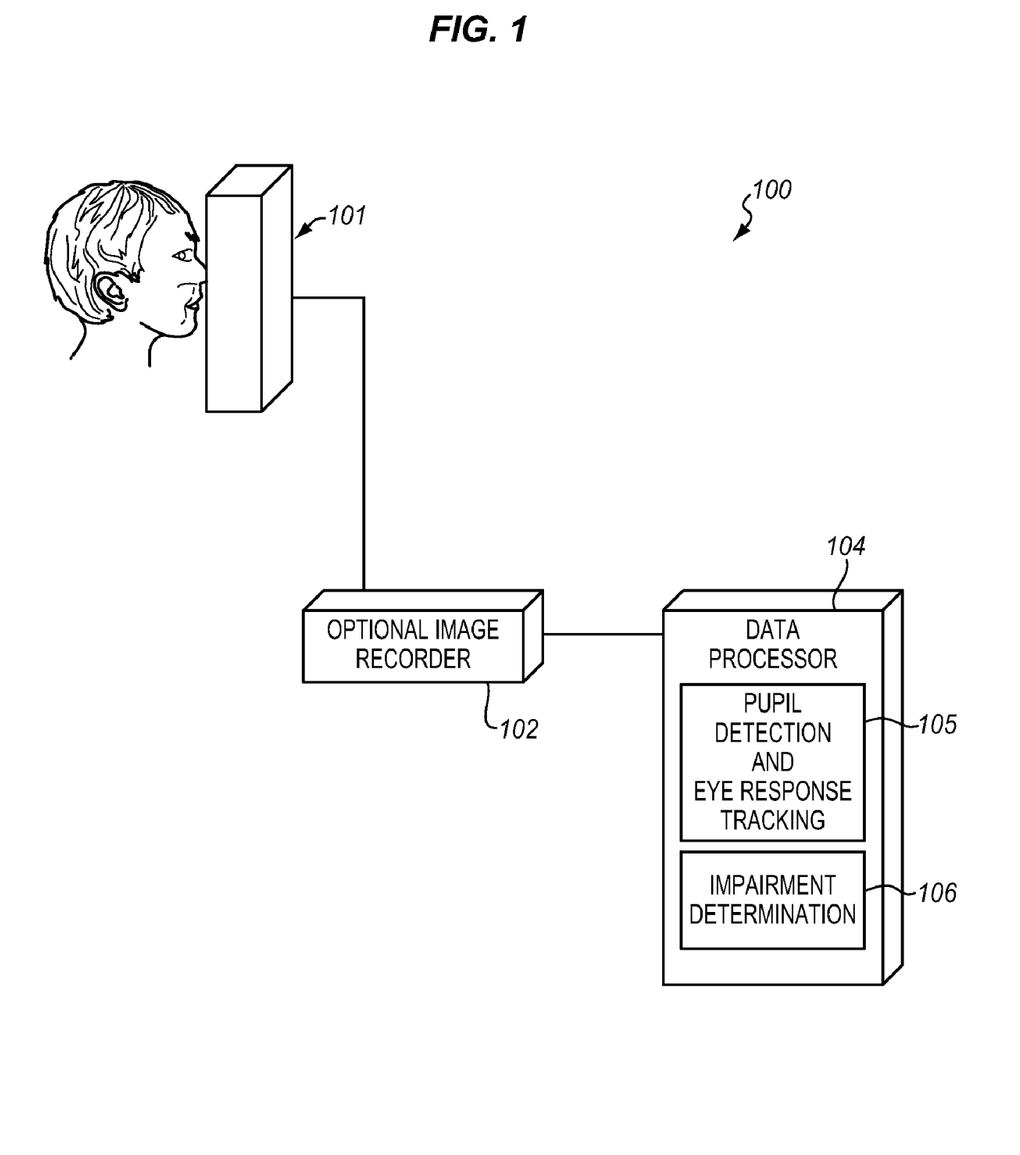
FIG. 1 illustrates a block diagram of the present pupil tracking system which is implemented as part of an impairment determination system.

FIG. 1 illustrates a block diagram of the present pupil tracking system 105 which is implemented, for example, as part of an impairment determination system 100, where a user interface 101 is used to administer the predetermined test protocol to the subject. The use of the impairment determination system illustrates the operation of the present pupil tracking system and provides a practical example of the benefits of this system, and is not intended to limit the scope of the appended claims. In this application, the user interface 101 can be a device, such as that shown in the above-mentioned U.S. Pat. No. 5,137,345, which includes illumination devices (not shown), imaging devices (not shown), and apparatus (not shown) to position the subject's face with respect to the illumination devices and imaging devices. To detect movement of the eye in response to visible stimulus, illumination devices comprising a plurality of low intensity, visible light sources can be disposed horizontally and vertically within the user interface 101. The sequential illumination of the visible light sources simulates eye movement while precluding pupil reaction thereto. Alternatively, the subject's eye movement can simply be tracked and then compared to normal eye movement and/or eye movement of the subject in a previously administered test to make an accurate determination of the subject's condition. A source of electrical power, such as batteries, is provided to power the illumination devices and imaging devices. The imaging devices can be connected to an image recording device 102 for capturing and storing image data if a record of the images is desired. The interconnection between the user interface 101 and the image recording device 102 can be wired or wireless, using a cable or wireless communication protocol, respectively.

In addition, a data processing system 104 processes the received images using the pupil tracking system 105. The received images are processed by a frame capture apparatus included in the data processing system 104 to form a timewise sequence of digital image frames indicative of the subject's eye responses. The present pupil tracking system 105 performs an analysis of the digital image frames generated by the imaging devices as they are received to quickly and accurately localize the pupil's boundaries, area, and center coordinates in close-up digital imagery of the subject's eye(s) as captured with the imaging devices. The pupil tracking system 105 uses a region-growing eye-response tracking process to extract and track the centroid location and area of the subject's pupil under difficult conditions, such as blinking, eyelid droop, head movement, eye gaze at the extreme corners of the eyes, presence of heavy eye makeup, and where light specularities occur in or near the pupil region.

An impairment determination process 106 can be used, for example, to take the pupil area, location and movement output data from the present pupil tracking system 105 to determine impairment of the subject. The impairment determination process 106, for example, can maintain one or more test protocols that consist of a series of stimuli which follow a predefined pattern. The impairment determination process 106 also maintains one or more test responses, indicative of a normal eye movement response or the subject's normal eye movement response to a corresponding test stimulus, as determined during a previously administered test on the subject. By matching the measured response of the subject to a given test protocol with normal responses, the impairment determination process 106 can make an accurate determination of whether the subject is impaired. Since it is impossible for a subject to maintain a uniform level of impairment, the comparison of present test results to prior test results ensures that any significant departure from the norm for this subject is detected.

Figure 4:
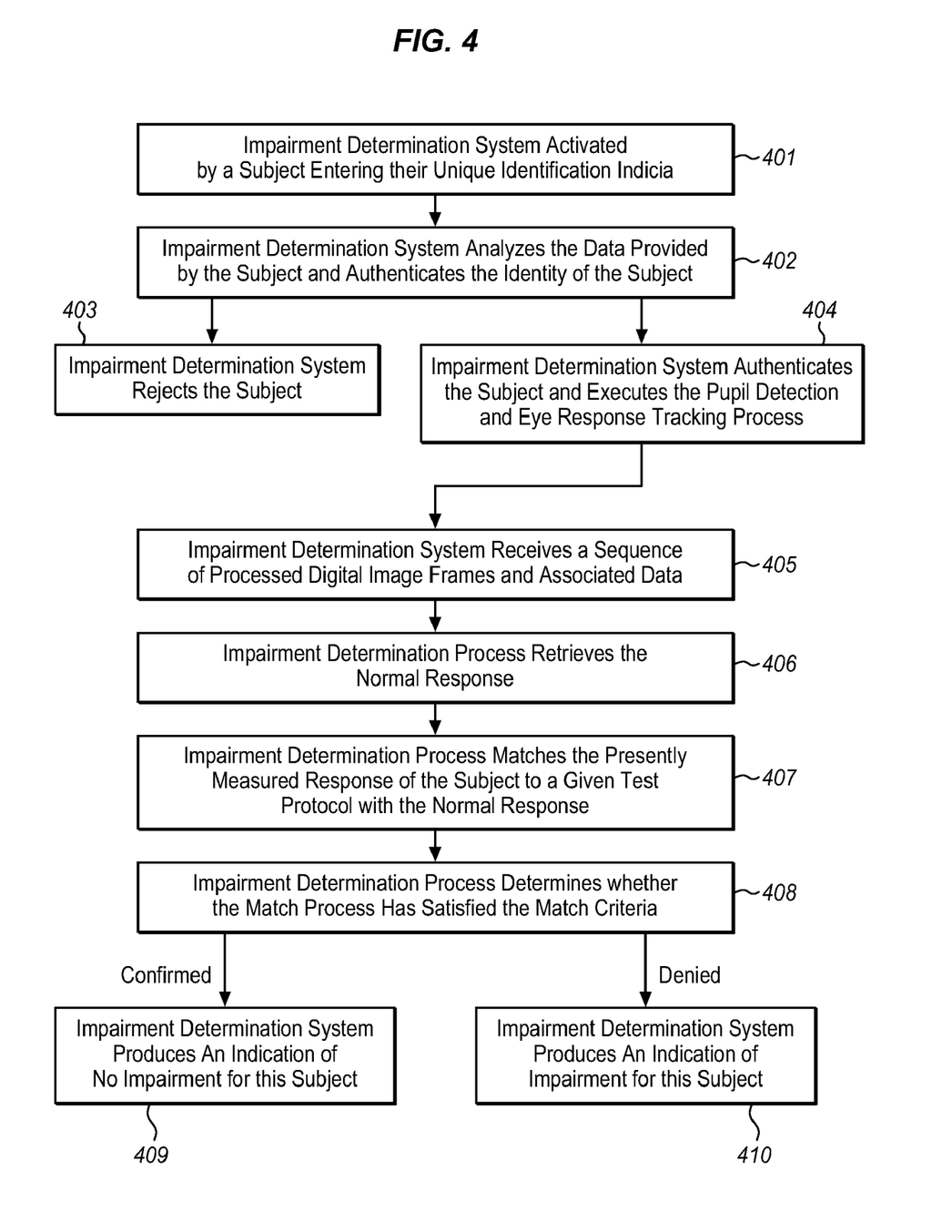
FIG. 4 illustrates, in flow diagram form, the operation of an impairment determination process which uses the pupil location and movement data generated by the present pupil tracking system.

FIG. 4 illustrates, in flow diagram form, the operation of the impairment determination process, inclusive of the operation of the present pupil tracking system 105. The impairment determination system 100 is activated at step 401 by a subject entering their unique identification indicia via a keypad, scanner device, wireless interface, etc., to distinguish this subject from others. The authentication of the subject can include a subject specific password and/or the scanning of an immutable physical characteristic of the subject, such as a fingerprint, iris scan, voiceprint, etc. The impairment determination system 100 at step 402 analyzes the data provided by the subject and authenticates the identity of the subject based on previously stored identification criteria that have been stored for this subject. If there is a failure to match the subject with the stored identification criteria, the impairment determination system 100 rejects the subject at step 403 and generates an alarm indication that the subject is not a valid user. A match results in the impairment determination system 100 proceeding at step 404 to activate the pupil tracking system 105 as is described below. The collection of this data is a condition precedent to the operation of the impairment determination process 106, which is described below.

Operation of the Pupil Tracking System

Figure 2:
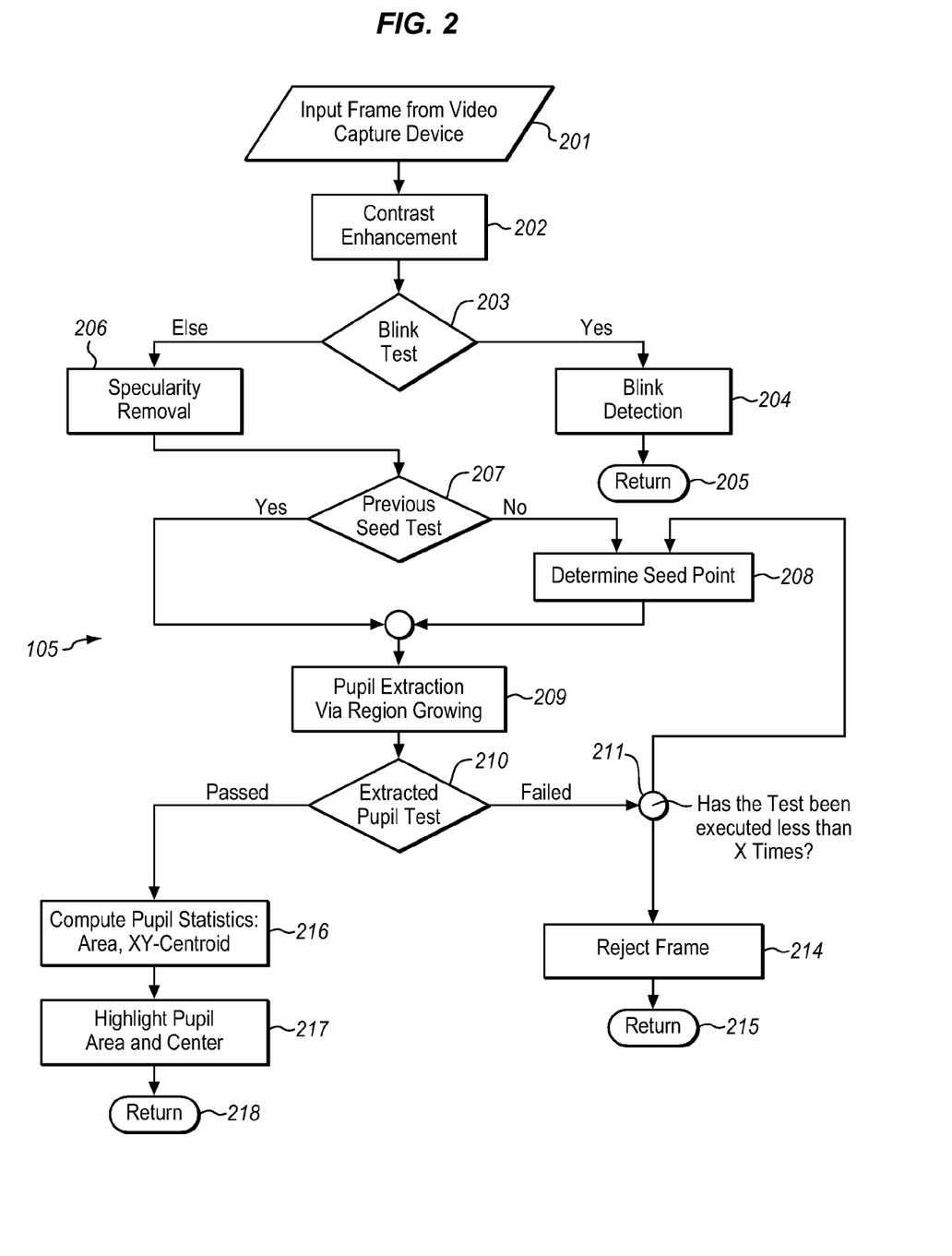
FIG. 2 illustrates, in flow diagram form, the operation of the present pupil tracking system.

FIG. 2 illustrates, in flow diagram form, the operation of the pupil tracking system 105 which processes each digital image frame in a sequence of digital image frames received from the video capture device and outputs data indicative of the pupil area and location, such as the digital image frame with the pupil boundary highlighted and with crosshairs delineating the pupil centroid location.

The video capture device generates a time sequence of digital image frames, each of which is an image of at least one of the subject's eyes. The video capture device can create a single image of one eye, or both eyes, or paired image frames of the eyes, and the pupil tracking system 105 may track the pupil in one or both of the subject's eyes. The present description refers to the processing of an image of one of the subject's eyes as the common descriptive example that is used for simplicity's sake and is intended to include all possible combinations of eye imaging and frame generation in all of these possible scenarios.

Figure 3A:
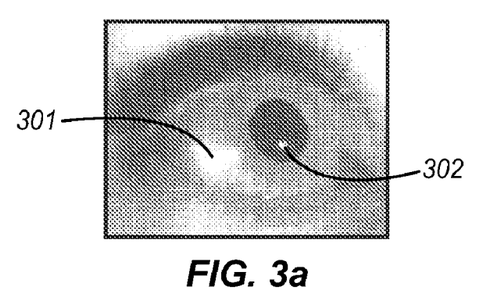
FIG. 3a illustrates a typical image of a subject's eye.

The pupil tracking system 105 operates in the following manner. A digital image frame, as shown in FIG. 3*a*, from the video capture device is input to the process at step 201. This received digital image frame is processed by providing contrast enhancement at step 202 to improve the quality of the received image and then performing, at step 203, a blink test to determine whether the subject is blinking in this digital image frame. If a blink is detected at step 203, then an indication of a blink is produced at step 204, processing of this digital image frame by the pupil tracking system 105 concludes and, at step 205, processing returns to step 201 to proceed with the next successively received image in the received sequence of digital image frames.

Figure 3B:
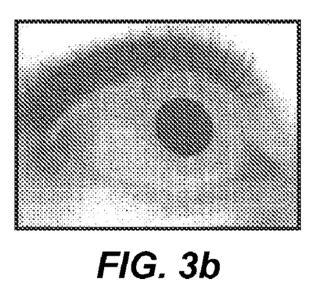
FIG. 3b illustrates the image of FIG. 3a with specularities removed.
Figure 3C:
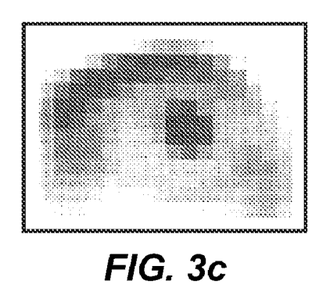
FIG. 3c illustrates a block summed version of the image of 3b.

If no blink is detected, then the digital image frame is first processed at step 206 where bright specularities, such as 301 and 302 shown in FIG. 3*a*, in the image are filled in, as shown in FIG. 3*b*, to reduce their effect on the subsequent processing. It is then determined at step 207 whether this is the first digital image frame in a sequence and whether a seed point has been previously determined. If a seed point has been previously determined, processing advances to step 209 where the previously determined seed point is used but, if not, the process computes a seed point at step 208 and processing advances to step 209. The candidate seed points are identified by finding the darkest point in a coarsely encoded image, as shown in FIG. 3*c*, that is computed by summing the intensities in each 20×20 block of pixels in the digital image frame. Next, a region-growing method is applied at step 209 at the best candidate seed point (x, y), which is indicated as 303 in FIG. 3*d*, to extract the subject's pupil from the image. If the first extracted region as computed in step 209 fails the pupil geometry tests (e.g., is the extracted region circular?) as determined at step 210, at step 211 the system determines whether the process has exceeded the allowable number of cycles of this test. If it has not, processing returns to step 208 where the best alternate candidate seed point (x', y') is selected and the region-growing method is applied at step 209. If this cycle fails the pupil geometry test as determined at step 210, the digital image frame is rejected at step 214 and processing returns at step 215 to step 201, where the next digital image frame in the sequence is obtained.

Generally, the first seed point lies within the pupil region, so the alternative seed point is rarely used. In addition, if a blink or eye-view change did not occur in the previous frame, the previously determined pupil centroid location is used at step 207 as the best candidate seed point in order to speed up the processing.

Figure 3D:
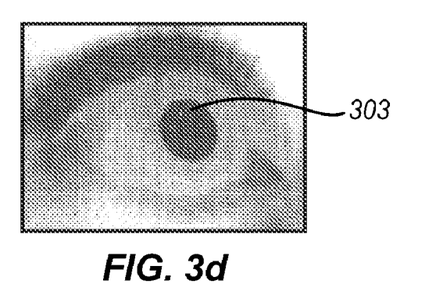
FIG. 3d illustrates the image of FIG. 3b with candidate seed points indicated.
Figure 3E:
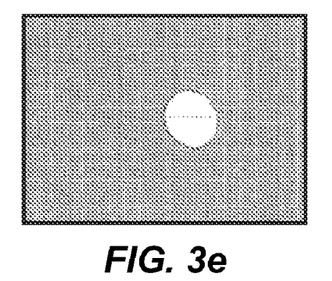
FIG. 3e illustrates the image of FIG. 3d with growing pupil extraction.
Figure 3F:
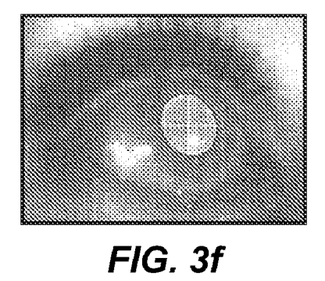
FIG. 3f illustrates the final image of the eye with the final pupil boundary and centroid results.

Finally, an ellipse is fitted over the extracted pupil region at step 216 to smooth the contours of the pupil boundary, and then the pupil XY-centroid location and pupil area measurements are computed. The pupil area then is highlighted on the image, and the pupil centroid location is indicated in the image, as shown in FIG. 3*f* at step 217. Processing of this image then concludes at step 218, and the process returns to step 201 to determine if there is another digital image frame in the sequence of received digital image frames.

Pupil Contrast Enhancement

As noted above, the pupil tracking system 105 at step 202 performs a contrast enhancement process to improve the quality of the received image. Contrast enhancement is needed in cases where poor lighting conditions exist, such as the image darkening and blur that often occurs when the subject focuses their attention towards the extreme corners of the eye. Enhancing the contrast between the pupil's edge and the iris of the eye helps to segment the pupil from the rest of the eye. A non-linear contrast adjust approach can be used to rescale the distribution of intensities to enhance edge boundaries.

Blink Detection

As noted above, the pupil tracking system 105 at step 203 performs a blink test. Frames that are part of a blinking motion should not be processed, since the pupil is either partially visible or not visible at all in the image frames where the subject is blinking. These images would produce erroneous pupil location data which corrupts the test results and could result in a false determination of impairment. Therefore, two preliminary blinking tests are performed on each image frame before they are processed and considered to be valid eye frames. These initial blinking tests are as follows:

1. Chi-Squared Statistical Test: Compute the distribution of intensities (i.e., the grayscale histogram) of the present frame and compare its results with the histogram obtained from the previous digital image frame. Drastic changes in the distributions between adjacent digital image frames are reflected by high Chi-Squared statistics, signaling the starting or ending of a blink, or the change in the camera view from one eye to the other. Letting X be the histogram of frame t and Y be the histogram of frame t+1, then the Chi-Squared statistic may be computed as:

$$d\chi^2(X, Y) = \frac{1}{2}\sum_{i=1}^{N} \frac{(X_i - Y_i)^2}{(X_i + Y_i)}$$

2. Low Intensity Distribution Test: An image containing a very low maximum intensity is either a blank frame (all black), or a very dark image with poor lighting, which does not provide the necessary contrast information needed to properly extract the pupil. This condition may occur if the subject's face is not firmly pressed up to the visor at the start of the test protocol or if they suddenly pull away during testing. Therefore, digital image frames with extremely low maximum intensity values are discarded.

Once a digital image frame is considered to be part of a blink movement, flags are set to disable further processing, and the output is a digital image frame with a white horizontal bar extending across the width of the image indicating that a blink has been detected.

Specularity Removal

As noted above, the pupil tracking system 105 at step 206 removes specularities from the received digital image frame. If a digital image frame contains light specularities occluding parts of the pupil, this disrupts the pupil's viewable area and, thus, interferes with the accuracy of the pupil measurements. For uses of this data, such as the determination of impairment, it is critical that the measurements be consistent and precise; therefore, all of the light specularities or bright areas should be removed from the image prior to finding the pupil and computing the statistics. Bright spots are detected by thresholding and then filling in the holes using bilinear interpolation of the surrounding pixels. An example is shown in FIG. 3a, which illustrates the original image with specularities in the pupil region, while FIG. 3b illustrates the image after the system removes the specularities.

Seed Point Determination

To speed up the algorithm, the pupil centroid that was computed in the previous digital image frame is used as a seeding point for the present digital image frame, since the eye does not move significantly in the interval between successive frames of the series of digital image frames. If the previous digital image frame is unavailable, the candidate seed point is selected by searching for the darkest point in an image formed by summing the intensities in each 20×20 pixel image block. FIG. 3c shows the image that is formed using this procedure, and FIG. 3d illustrates the best seed point. When the region extracted using the best candidate seed point is determined to be non-pupil like, all blocks in the summed image near the seed point are masked out by increasing their intensity values, and the next darkest seed point is determined. The above-described process of growing the region and testing the geometry is repeated, but if the process fails for the second time, the digital image frame is rejected.

Pupil Extraction Via Region Growing

Having selected a seed point, a region is grown around the seed point using a region-growing algorithm designed to search for and include pixels in the boundary that are of similar color and intensity. The growth is halted at the strong edge boundaries where the pupil and iris meet. The following cost function is used for this process:

$$C(x, y) = \gamma e^{\frac{(I(x,y)-\mu_0)^2}{2\sigma_0^2}} + (1-\gamma)\frac{1}{1 + |\nabla I(x, y)|^p}$$

where $\mu_o$ and $\sigma_o$ are the mean and standard deviation near the seed point, and p and $\gamma$ are parameters determined empirically. This approach extracts the exact shape of the pupil, which is critical for the accurate computation of the pupil area and centroid location measurements.

Region Geometry Test

As noted above, the pupil tracking system 105 at step 209 performs a pupil geometry test. After extracting a region, the process must make sure that it corresponds to the pupil and not to some other dark region in the digital image frame, such as the eyelashes, the eyebrows, or the corners of the eye. Therefore, the extracted region is tested for its perimeter, roundness, and circularity. These geometric features provide a measurement of how large and elliptical the extracted boundary is. Regions with very small area and/or non-elliptical are classified as not being part of the pupil and are discarded from further analysis. The perimeter is computed as the length of the boundary, and the roundness and circularity measures are computed as:

$$\text{Roundness} = \frac{|\text{Perimerter}|^2}{\text{Area}}$$

and $$\text{Circularity} = \frac{\mu_R}{\sigma_R}$$

where $\mu_o$ and $\sigma_o$ are the mean and standard deviation of the radial distance from the centroid location to the shape of the boundary.

Compute Pupil Measurements

As noted above, the pupil tracking system 105 at step 216 determines the characteristics of the detected pupil. If the extracted region is considered to be the pupil, its contour is smoothed by fitting an ellipse to the region, and then the process computes the area and XY-centroid location of the final boundary. The pixels corresponding to the extracted pupil region are highlighted, and cross-hairs are drawn at the coordinates of the pupil's centroid location. The pupil area and XY-centroid location are stored for use in the determination of impairment.

Impairment Determination Process

Upon completion of the image data processing by pupil tracking system 105, impairment determination system 100 at step 405 can optionally store a sequence of processed digital image frames, each of which contains highlighted pixels corresponding to the extracted pupil region, and cross-hairs drawn at the coordinates of the pupil's centroid location, in a memory. The data indicative of pupil area and XY-centroid location can also optionally be stored for use in the determination of impairment. The impairment determination process 106 uses this pupil area and location data to determine whether a subject is impaired, regardless of whether caused by a medical condition, or the use of alcohol or drugs, or the subject is suffering from sleep deprivation, or any other condition which interferes with the subject's ability to perform their assigned tasks.

The impairment determination process 106 maintains one or more test protocols that define a set of test stimuli which typically consists of a target which follows a predefined pattern. The impairment determination process 106 also maintains one or more test responses, indicative of a normal eye response or the subject's normal eye movement response to a corresponding set of test stimuli, as determined during a previously administered test on this subject. At step 406, the impairment determination process 106 retrieves the normal test results. By matching the presently measured response of the subject to a given test protocol at step 407 with the normal responses, the impairment determination process 106 can make an accurate determination of the subject's impairment. The matching can be based on an algorithmic computation of the subject's pupil location in each digital image frame of the successive digital image frames and the size of their pupil, or it can be a point-matching protocol to determine whether the pupil movement tracks within a predetermined range of movement. In any case, the delay in the subject's eyes responding to the test stimulus and the accuracy of the pupil movement in following the test stimulus, combined with pupil size, provide a precise determination of impairment. Thus, at step 408, the impairment determination process 106 determines whether the match process executed at step 407 has satisfied the match criteria and, if a match is confirmed, at step 409 the impairment determination system 100 produces an indication of no impairment for this subject. However, if the match process executed at step 407 fails to satisfy the match criteria, the impairment determination system 100 produces an indication of impairment for this subject at step 410.

SUMMARY

The present system for analyzing eye responses accurately and automatically tracks the size, location, and movement of a subject's pupil(s) in response to predetermined stimuli. These eye responses include both ocularmotor and pupillary responses to illumination and target tracking for either eye or both eyes simultaneously. The series of digital image frames of a subject's eyes, taken during the execution of a predetermined test protocol, are automatically processed to determine pupil location, size, and responsiveness to changes in illumination.

What is claimed as new and desired to be protected by Letters Patent of the United States is:

1. A pupil tracking system for automatically determining pupil responses, as recorded in a time-wise sequence of digital images of at least one of the subject's eyes, comprising:
digital image processing means for identifying a location of a pupil of at least one of said subject's eyes in a plurality of said digital images in said sequence of digital images, comprising:
center point determining means for identifying a darkest spot in the pupil of said eye, pupil geometry determining means for ensuring said pupil satisfies a minimum shape configuration, comprising:
region-growing means for applying a region-growing procedure to said identified darkest spot of said pupil to expand the boundaries of said pupil to include regions of equivalent decreasing darkness; and
pupil size means for computing a size of said pupil in said plurality of said digital images in said sequence of digital images.

2. The pupil tracking system of claim 1 further comprising:
pupil movement determining means, responsive to data indicative of said location of said pupil, for tracking eye movement in said plurality of digital images.
3. The pupil tracking system of claim 1 further comprising:
filtering means for removing light specularities from said digital image.
4. The pupil tracking system of claim 1 wherein said pupil geometry determining means further comprises:
shape means for fitting an ellipse over the extracted pupil region to smooth the contours of the boundary.
5. The pupil tracking system of claim 4 wherein said pupil geometry determining means further comprises:
editing means for discarding regions with very small area or not being included within an elliptical shape from further analysis.
6. The pupil tracking system of claim 4 wherein said pupil geometry determining means further comprises:
geometric feature determining means for testing said pupil for at least one of its perimeter, roundness, and circularity.
7. The pupil tracking system of claim 6 wherein said geometric feature determining means comprises:
computation means for computing the perimeter of said pupil as the length of the boundary, and the roundness and circularity measures as:

$$\text{Roundness} = \frac{|\text{Perimerter}|^2}{\text{Area}}$$

and $$\text{Circularity} = \frac{\mu_R}{\sigma_R}$$

where $\mu_o$ and $\sigma_o$ are the mean and standard deviation of the radial distance from the center of the pupil to the shape of the boundary.
8. The pupil tracking system of claim 1 further comprising:
blink determining means for rejecting a digital image when a distribution of intensities of the current digital image drastically changes from the distribution of intensities obtained from the previous digital image.
9. A method for automatically determining pupil responses, as recorded in a time-wise sequence of digital images of at least one of the subject's eyes, comprising:
identifying a location of a pupil of at least one of said subject's eyes in a plurality of said digital images in said sequence of digital images, comprising:
identifying a darkest spot in the pupil of said eye,
ensuring said pupil satisfies a minimum shape configuration, comprising:
applying a region-growing procedure to said identified darkest spot of said pupil to expand the boundaries of said pupil to include regions of equivalent decreasing darkness; and
computing a size of said pupil in said plurality of said digital images in said sequence of digital images.
10. The method for automatically determining pupil responses of claim 9 further comprising:
tracking, in response to data indicative of said location of said pupil, for tracking eye movement in said plurality of digital images.
11. The method for automatically determining pupil responses of claim 9 further comprising:
removing light specularities from said digital image.

12. The method for automatically determining pupil responses of claim 9 wherein said step of ensuring further comprises:

fitting an ellipse over the extracted pupil region to smooth the contours of the boundary.

13. The method for automatically determining pupil responses of claim 12 wherein said step of ensuring further comprises:

discarding regions with very small area or not being included within an elliptical shape from further analysis.

14. The method for automatically determining pupil responses of claim 12 wherein said step of ensuring further comprises:

testing said pupil for at least one of its perimeter, roundness, and circularity.

15. The method for automatically determining pupil responses of claim 14 wherein said step of testing comprises:

computing the perimeter of said pupil as the length of the boundary, and the roundness and circularity measures as:

$$\text{Roundness} = \frac{|\text{Perimerter}|^2}{\text{Area}}$$

and $$\text{Circularity} = \frac{\mu_R}{\sigma_R}$$

where $\mu_o$ and $\sigma_o$ are the mean and standard deviation of the radial distance from the center of the pupil to the shape of the boundary.

16. The method for automatically determining pupil responses of claim 9 further comprising:

rejecting a digital image when a distribution of intensities of the current digital image drastically changes from the distribution of intensities obtained from the previous digital image.

* * * * *